United States Patent [19]

Kreutzer

[11] 4,154,779

[45] May 15, 1979

[54] SULPHURIZED PHOSPHORIC ACID ESTER SALTS AND METHOD OF PREPARATION

[75] Inventor: Ingo Kreutzer, Oftersheim, Fed. Rep. of Germany

[73] Assignee: Rhein-Chemie Rheinau GmbH, Mannheim, Fed. Rep. of Germany

[21] Appl. No.: 770,148

[22] Filed: Feb. 18, 1977

[30] Foreign Application Priority Data

Mar. 4, 1976 [DE] Fed. Rep. of Germany ....... 2608836

[51] Int. Cl.$^2$ .......................... C07F 9/09; C10M 1/44
[52] U.S. Cl. .................................. 260/924; 252/32.5; 252/46.4; 252/46.7; 260/125; 260/987
[58] Field of Search ........................ 260/924, 125, 987

[56] References Cited

U.S. PATENT DOCUMENTS

| | | | |
|---|---|---|---|
| 2,502,408 | 4/1950 | Adelson | 260/125 X |
| 3,471,404 | 10/1969 | Myers | 260/139 X |

OTHER PUBLICATIONS

Strausz, "Organosulfur Chemistry", Interscience Publishers, New York, (1968), pp. 20–21.
Bateman et al, "Organic Sulfur Compounds", vol. 1, Pergamon Press, New York, (1961), pp. 210–211.

*Primary Examiner*—Anton H. Sutto
*Attorney, Agent, or Firm*—Sprung, Felfe, Horn, Lynch & Kramer

[57] ABSTRACT

Sulpherized monoalkylphosphoric acid mono-salts are prepared by sulphurization of an alkylene group, phosphorylation and subsequent neutralization. Said products are excellent high pressure additives and corrosion inhibitors.

10 Claims, No Drawings

SULPHURIZED PHOSPHORIC ACID ESTER SALTS AND METHOD OF PREPARATION

The requirements to be met by high pressure oils used for the lubrication of gears and hydraulic installations and in the treatment of metals are constantly becoming more exacting owing to the ever more compact construction of machine elements combined with the transmission of greater forces and more rapid manufacturing methods.

The high pressure oils currently used, which are alloyed with various combinations of compounds of lead, chlorine, phosphorus and sulphur, now only partly fulfil the requirements of freedom from ash, greater protection against seizing and less wear and more favourable corrosion characteristics even at high temperatures, particularly since chlorine compounds must be eliminated on account of their corrosiveness and lead compounds on account of their harmful effects on the environment. High pressure oils already proposed which are alloyed with phosphorus and sulphur additives also only partly meet the somewhat contradictory requirements, the main defects being their insufficient protection against seizing and insufficient temperature resistance.

It is an object of the present invention to provide an additive for high pressure oils which will meet these requirements.

The invention relates to monoalkylphosphoric acid mono-salts of the formula

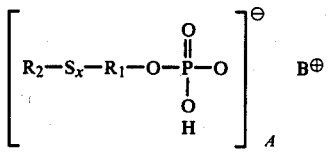

wherein
x represents a number of from 1 to 5, preferably 2 or 3,
B denotes a metallic or aminic cation,
A represents the valency of B, preferably a value of from 1 to 3, and
$R_1$ and $R_2$, which may be identical or different, denote straight chain, branched chain or cyclic, saturated or unsaturated, hydrocarbon groups having from 3 to 30 carbon atoms which may be substituted by one or more of the following groups:
—OH, —COOH, —COOR$_6$, —OOCR$_6$, —OR$_6$, [—O—PO(OH)—O]$^-$B$^+$, —S$_x$—R$_6$.

The invention also has as its object a process for the preparation of the compounds and the use of the compounds as lubricant additives in mineral or synthetic oils, optionally in combination with already known lubricant additives.

The metal cations used may be elements from the 1st to 5th Main Group, preferably Li, Na, K, Mg, Ca, Ba, Al, Sn, Pb, Sb or Bi or from the 1st to 3rd or 5th to 8th sub-Group, preferably Cr, Mn, Fe, Co, Ni, Cu, Zn, Mo or Cd. B$^+$ may also represent an optionally substituted ammonium ion of the following formula:

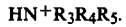

In this formula, $R_3$–$R_5$ may be hydrogen and/or identical or different straight chain or branched chain alkyl groups or cycloalkyl groups having from 1 to 30 C-atoms, optionally substituted with ether, alcohol, amine or alkylamine groups, or two of the radicals $R_3$ to $R_5$ may be linked to form a heterocyclic group with the N-atom. Among the amines, the following are preferred: Mono-, di- and trialkylamines of methylamine, ethylamine, propylamine, isopropylamine, butylamine, isobutylamines, secondary butylamine, tertiary butylamine, pentylamine, isopentylamines, cyclopentylamine, hexylamine, isohexylamines, cyclohexylamine, heptylamine, isoheptylamines such as 1,4-dimethylpentylamine, 5-methylhexylamine, methyl cyclohexylamine, octylamine, isooctylamines such as diisobutylamine and 2-ethylhexylamine, nonylamine, isononylamines such as tripropylamine, decylamine, isodecylamines, undecylamine, isoundecylamines, laurylamine, isododecylamines such as tetrapropylamine, triisobutylamine, tridecylamine, myristylamine, pentaisopropylamine, palmitylamine, tetraisobutylamine, stearylamine, oleylamine, hexaisopropylamine, arachylamine, pentaisobutylamine, heptapropylamine, behenylamine, erucylamine, octapropylamine, nonapropylamine, heptaisobutylamine and decapropylamine;

mixed substituted alkylamines such as N-methyl-2-ethylhexylamine, N-methyl-sec.-butylamine, N,N-dimethyl-2-ethylhexylamine, N-butyl-2-ethylhexylamine, N,N-dibutyl-2-ethylhexylamine, N-methylstearylamine, N,N-dimethyl palm kernel fatty amine, N-methyl-cyclohexylamine, dimethylcyclohexylamine, diethylcyclohexylamine, 2-methoxymethylamine, di-2-methoxy-methylamine, 2-ethoxymethylamine, 3-methoxypropylamine, 3-ethoxypropylamine, 3-isopropoxypropylamine, 2-butoxyethylamine and 3-(2-ethylhexoxy)-propylamine;

ethylenediamine, propylene-1,2-diamine, 1,3-diaminopropane, 1,4-diaminocyclohexane, 1,4-diaminobutane, diethylenetriamine, triethylene tetramine, tetraethylene pentamine, pentaethylene hexamine, polyethyleneamine, 2-amino-1-diethylaminoethane, 3-amino-1-methylaminopropane, dimethylaminopropylamine, diethylaminopropylamine, N,N,N',N'-tetramethylethylenediamine, N,N'-dimethyl-N,N'-bis-(aminopropyl)-ethylenediamine, 1-diethylamino-4-aminopentane, nonadecanodiamine, bis-(3-aminopropyl)-methylamine, 3,3'-diaminodipropylamine, 2,2'-diaminodipropylamine, 2-aminomethylcyclopentylamine, 3-cyclohexylaminopropylamine, 4,4'-diaminocyclohexylmethane, 3,3'-dimethyl-4,4'-diaminodicyclohexylmethane, 2,2-bis-(4-aminocyclohexyl)-propane, 2-amino-1-dimethylaminoethane, 3-amino-1-dibutylaminopropane, 3-amino-1-stearylaminopropane, bis-(6-aminohexyl)-amine, 1,2-bis-(3-aminopropylamino)-ethane and 1,6-bis-(3-aminopropylamino)-hexane;

monoethanolamine, diethanolamine, triethanolamine, dimethylethanolamine, monoethylethanolamine, aminoethylethanolamine, diethylethanolamine, butylethanolamine, dibutyl ethanolamine, methyldiethanolamine, ethyldiethanolamine, n-butyl-diethanolamine, methyldiisopropanolamine, dimethylisopropanolamine, butyldiisopropanolamine, diisopropanolamine, triisopropanolamine, N,N-diethyl-ethoxy-ethanolamine, 2-(2-hydroxyethoxy)-1-ethylamine, N-methyl-N-(3-aminopropyl)-ethanolamine, 3-aminopropanol, 3-dimethylaminopropanol, cyclohexylethanolamine, cyclohexylisopropanolamine, cyclohexyldiisopropanolamine and cyclohexyldiethanolamine;

pyrrolidine, 1-methylpyrrolidine, 1-ethylpyrrolidine, piperidine, 1-methyl-piperidine, 1-ethylpiperidine, 1-(2- hydroxyethyl)-piperidine, 1-(3-amino-propyl)-piperidine, hexamethyleneimine, N-methylhexamethyleneimine, morpholine, N-methylmorpholine, N-ethylmorpholine, N-butylmorpholine, N-stearylmorpholine, N-cyclohexylmorpholine, 4-(2-hydroxyethyl)-morpholine and 4-(3-aminopropyl)-morpholine.

$R_1$ and $R_2$ are identical or different and denote straight chain, branched chain or cyclic, saturated or unsaturated, hydrocarbon groups having from 3 to 30 C-atoms and optionally substituted with one or more of the following groups:

—OH, COOH, —COOR$_6$, —OOCR$_6$, —OR$_6$,
[—O-PO(OH)—O]$^-$B$^+$, —S$_x$—R$_6$ wherein $R_6$ denotes methyl, ethyl, $R_1$ or $R_2$ and x represents a value of from 1 to 5, preferably 2 or 3.

$R_1$, $R_2$ and $R_6$ are radicals of methane, ethane, propane, butane, pentane, hexane, heptane, octane, nonane, decane, undecane, dodecane, tridecane, tetradecane, pentadecane, hexadecane, heptadecane, octadecane, nonadecane, eicosane, heneicosane, docosane, tricosane, tetracosane, pentacosane, hexacosane, heptacosane, octacosane, nonacosane or tricontane, or their structural isomers. They may be substituted with alcohol groups, carboxylic acid groups, ester groups, ether groups, phosphoric acid mono-salt groups or thio or polythio alkyl groups.

Preparation of the sulphurised monoalkyl phosphoric acid mono-salts is carried out in several stages with possibilities of variation: sulphurisation of the alkyl group, phosphorylation and neutralisation carried out in any desired sequence, except that neutralisation must take place after phosphorylation.

This means that sulphurisation may be carried out either on an unsaturated hydrocarbon, alcohol or alkyl halide or on the monoalkyl phosphoric acid prepared from it or on its mono-salts, optionally mixed with other unsaturated hydrocarbons, esters, ethers or acids.

Sulphurisation may be carried out by reaction of the unsaturated components with sulphur chloride followed by treatment with sodium sulphide, or by direct sulphurisation with elementary sulphur.

When sulphur chloride is used for sulphurisation, preferably half of a mol of sulphur chloride is slowly added per double bond to the unsaturated compounds at a temperature of from 0° to 100° C. with stirring. Stirring is then continued for a little while before 1 mol of sodium sulphide dissolved e.g. in methanol is slowly added per mol of sulphur chloride. The chlorine split off in the reaction precipitates as NaCl and is filtered off. A suitable product is obtained after evaporation of the solvent.

In the process of direct sulphurisation, the unsaturated compounds together with 1 to 2 mol of sulphur and optionally a catalyst, e.g. an amine, are preferably heated to 120°-200° C. for 1 to 10 hours with stirring. Air is then blown through the reaction mixture for 1 to 3 hours at about 80° C.

Unsaturated alcohols such as the following are suitable for direct sulphurisation: allyl alcohol, butenol such as buten-1-ol-3, pentenols such as 3-methylbuten-3-ol-1, 3-methylbuten-2-ol-1 or 2-methylbuten-3-ol-2, hexenols, heptenols, octenols, nonenols, decenols, undecenols, dodecenols, tridecenols, tetradecenols, pentadecenols, hexadecenols, heptadecenols, octadecenols, nonadecenols, eicosenols, heneicosenols, docosenols, tricosenols, tetracosenols, pentacosenols, hexacosenols, etc. and particularly fatty alcohols such as laurystoleyl alcohol, palmitoleyl alcohol, oleyl alcohol, elaidyl alcohol, linolyl alcohol, linolenyl alcohol, elaeostearyl alcohol, arachidonyl alcohol, erucyl alcohol, clupanodonyl alcohol, castor oil, ricinoleic fatty acid and esters thereof, such as methyl, ethyl, propyl, butyl and glycol esters, and terpene alcohols.

Also suitable are the monoesters of unsaturated fatty acids with glycol, monoesters and diesters of unsaturated fatty acids with glycerol and trimethylolpropane and mono-, di- and triesters of pentaerythritol with unsaturated fatty acids. Suitable unsaturated fatty acids include acrylic acid, methacrylic acid, myristoleic acid, palmitoleic acid, oleic acid, elaidic acid, linoleic acid, elaeostearic acid, archidonic acid, erucic acid and clupanodonic acid, but particularly mixtures thereof obtained by lipolytic reactions such as rape oil fatty acid, soya fatty acid, linseed oil fatty acid, tallow fatty acid, sperm oil fatty acid, lard oil fatty acid, cottonseed oil fatty acid, etc. Among the esters, the following are preferred: mono-rape oil fatty acid glycol ester, mono-soya bean oil fatty acid glycol ester, mono-soya bean oil fatty acid glyceric ester, glycerinedioleate, trimethylolpropane dioleate and pentaerythritol trioleate. Unsaturated ethers of polyhydric alcohols such as glycol, glycerol and trimethylolpropane are also suitable. Examples are the ethers obtained by reacting unsaturated alcohols with ethylene oxide, such as ethylene glycol monooleyl ether, diethylene glycol monooleyl ether, trimethylolpropane diallyl ether and glyceromonooleyl ether.

The above mentioned unsaturated alcohols and halogenated hydrocarbons as well as olefinic hydrocarbons are suitable for sulphurisation with sulphur chloride. The following are suitable olefinic hydrocarbons: propene, butene, isobutene, pentene, isopentenes, cyclopentene, hexene, isohexenes such as dipropylene, cyclohexene, heptene, isoheptenes, octene, isooctenes such as diisobutylene, nonene, isononenes such as tripropylene, decene, isodecenes, dodecene, isododecenes such as tetrapropylene and triisobutylene, tridecene, isotridecenes, tetradecene, isotetradecenes, pentadecene, isopentadecenes, such as pentapropylene, hexadecene, isohexadecenes such as tetraisobutylene, heptadecene, isoheptadecenes, octadecene, isooctadecenes such as hexapropylene, nonadecene, isononadecenes, eicosene, isoheicosenes such as pentaisobutylene, heneicosene, isoheneicosenes such as heptapropylene, docosene, isodocosenes, tricosene, isotricosenes, tetracosene, isotetracosenes such as octapropylene and hexaisobutylene, and styrene.

Other unsaturated compounds which are suitable for mixed sulphurisation by the method of direct reaction with sulphur include the olefines already mentioned for sulphurisation with sulphur chloride. Substances which are suitable for mixed sulphurisation by either method include the unsaturated fats such as lard oil, rape oil, tallow, soya bean oil, sperm oil, linseed oil, cottonseed oil, sunflower oil, tall oil, fish oil and the fatty acids of these oils and their methyl, ethyl, propyl, butyl, isobutyl, glycol, trimethylolpropane and pentaerythritol esters.

Phosphorylation may also be carried out by various methods, using either an unsaturated alcohol or halide or a sulphurised alcohol or halide. The compounds on which phosphorylation may be carried out include both the raw materials described for the sulphurisation reaction and the sulphurised products.

Particularly suitable phosphorylating reactions are the reactions of alcohols with condensed phosphoric acids, phosphorus pentoxide, phosphorus oxychloride or phosphorus pentachloride followed by hydrolysis. Another method which may be used is the reaction of alkyl halides, in particular chlorosulphurised olefines, with phosphoric acid salts.

Phosphorylation of an alcohol is best carried out in an inert solvent in which the reaction product is soluble. Suitable solvents include e.g. ethers such as diethyl ether and dibutylether, hydrocarbons such as cyclohexane, hexane, petroleum hydrocarbons, benzene or toluene, and chlorine compounds such as trichloromethane, chloroform and 1,2-dichloroethane.

Phosphorylation is preferably carried out by introducing the solvent and the phosphorylating agent into the reaction vessel and adding 1 mol of alcohol per mol of phosphorus in the phosphorylating agent with stirring and either heating or cooling, depending on the reactivity of the components, the reaction temperatures employed generally ranging from 20° to 150° C., preferably 50° to 100° C. Hydrolysis is carried out after completion of the reaction, preferably by vigorous mixing with excess quantities of water at 20° to 100° C. It may also be carried out with aqueous solutions of basic compounds but in that case it is necessary to ensure that the formation of the salt which takes place at the same time does not go beyond the stage of the mono-salt.

Phosphorylation of alkyl halides is carried out using phosphoric acid salts or aqueous solutions thereof with vigorous stirring and heating at 50° to 200° C. After termination of the reaction, the inorganic phosphorus and halogen salts are separated off and the ester salts are converted into the free monoalkyl phosphoric acids or mono-salts by acidification with mineral acids.

Neutralisation of a free POH group of the monoalkyl phosphoric acid is carried out by simply mixing preferably stoichiometric quantities of phosphoric acid monoester and base at 20° to 150° C., preferably 60° to 100° C., liquid end products being obtained. Neutralisation is otherwise preferably carried out in solvents such as ethers, ketones, hydrocarbons, aromatic solvents, halogenated hydrocarbons, petroleum hydrocarbons or mineral oils. Neutralisation with metal bases may be carried out using either metal oxides or metal hydroxides or salts of weak and volatile acids such as metal carbonates. Conversion of certain salts may also be carried out by the so-called double reaction.

For certain technical reasons connected with the intended use of the products, e.g. compatibility with other alloying constituents and their ranges of activity such as bactericidal activity, high pressure properties or corrosion protective action, it may be desired to use acid or basic products. The quantity of base used may vary within wide limits outside the stoichiometric quantity, but preferably by not more than ±50%.

The sulphurised monoalkyl phosphoric acid monosalts are particularly suitable for use as high pressure additives and also as corrosion prohibitors when added to lubricants such as lubricant oils and greases in concentrations of from 0.01 to 20% by weight, preferably 0.2 to 5% by weight, based on the quantity of lubricant.

Suitable lubricants are those which have lubrication viscosities of from 5 to 3000 cSt at 50° C., preferably 10 to 300 cSt at 50° C., which include paraffinic, naphthenic, aromatic or mixed basic mineral oils and synthetic oils such as ester oils, ether oils, alkylbenzenes, hydrogenated olefine polymers and mixtures of the various lubricant oils.

The phosphoric acid ester salts according to the invention may be used either alone or in combination with other high pressure additives.

Other high pressure additives include the sulphur carriers known as high pressure additives, phosphorus compounds and compounds of phosphorus and sulphur, chlorine compounds and lead compounds.

Suitable sulphur carriers include sulphurised propylene and its oligomers such as di-, tri- and tetrapropylene, butylene and its oligomers, isobutylene and its oligomers, in particular sulphurised isobutylene, diisobutylene and tetraisobutylene, sulphurised α-olefines such as butene, pentene, hexene, heptene, octene, nonene, decene, undecene, dodecene, tridecene, tetradecene, pentadecene, hexadecene, octadecene, nonadecene, eicosene, heneicosene, docosene, tricosene, tetracosene, etc. but particularly mixtures thereof obtained from the cracking of paraffins; sulphurised cyclohexene and terpene and styrene; sulphurised fatty oils such as rape oil, linseed oil, soya bean oil, sunflower oil, lard oil, sperm oil and cottonseed oil; the sulphurised fatty acids of the above fatty oils and their methyl esters, ethyl esters, propyl esters, butyl esters and glycol esters. Sulphurised mixtures of the above mentioned raw materials for sulphurisation are particularly suitable, especially fatty oils mixed with olefines and fatty oils mixed with methyl esters of the fatty acids.

Suitable phosphorus compounds include the mono-, di- and tri-esters of phosphoric and phosphorus acid, such as dibutylphosphate, tributylphosphate, 2-ethylhexylphosphate, di-2-ethylhexylphosphate, tri-2-ethylhexylphosphate, tricresylphosphate, triphenylphosphite and tributylphosphite.

Suitable phosphorosulphur compounds include the salts of dialkyldithiophosphoric acids, such as zinc dialkyl dithiophosphates and lead dialkyldithiophosphates as well as salts of thiophosphoric acid triphenyl ester.

Suitable chlorine compounds include chloroparaffins and chlorosulphurated olefines and fatty oils.

Among the lead compounds should be mentioned the lead naphthenates.

The phosphoric acid ester salts according to the invention may be mixed with other high pressure additives in proportions ranging from 95:5 to 5:95, preferably from 20:80 to 80:20% by weight.

The lubricant oils may also contain other known lubricant oil additives such as antioxidants, corrosion prohibitors, anti-foaming additives, demulsifiers, metal inactivators and non-ferrous metal inhibitors.

Lubricants which have been mixed with the phosphoric acid ester salts according to the invention are particularly suitable for lubricating gears, such as spur gears and hypoid gears, and hydraulic installations and for the treatment of metals, but they are also suitable for many other special applications where high pressure properties are required. For example, they may be used as hammer oils, deep drawing oils, oils for bedways, drawing compounds, sliding greases and oils and greases for lubricating bearings.

The object of the invention will now be explained in more detail with the aid of the following Examples. All percentages and parts are by weight unless otherwise indicated.

EXAMPLE 1

100 g of oleyl alcohol, 100 g of rape oil, 25 g of sulphur and 0.1 g of dicyclohexylamine are heated to 150° C. under nitrogen with vigorous stirring in a round bottomed flask and stirring is then continued at this temperature for 5 hours. The mixture is cooled to 80° C. and blown out with air for 3 hours. A sulphur carrier with a 12% sulphur content is obtained which is suitable for phosphorylation.

100 g of the sulphur carrier are added slowly with stirring and cooling to a suspension of 26.5 g of phosphorus pentoxide in 100 ml of diethylether. The reaction mixture is boiled under reflux for one hour and 4 g of water are then added. After one hour's vigorous stirring, the ether is distilled off.

The reaction product obtained is the desired phosphoric acid monoester containing 9.3% of sulphur and 3.3% of phosphorus.

25.7 g of dioctylamine are added dropwise with stirring and cooling to 100 g of the sulphurised monoalkylphosphoric acid. The sulphurised monoalkylphosphoric acid monoamine salt is thereby obtained.

EXAMPLE 2

100 g of diisobutylene, 240 g of oleyl alcohol, 57 g of sulphur and 0.2 g of dicyclohexylamine are heated to 150° C. under nitrogen with vigorous stirring in a pressure vessel and then stirred for a further 5 hours at this temperature. The mixture is cooled to 80° C. and then blown out with air for 3 hours. A sulphur carrier containing 14.5% of sulphur is obtained.

100 g of the sulphur carrier are added to a solution of 34.4 g of phosphorus oxytrichloride in 100 ml of cyclohexane at 50° C. with stirring while a stream of nitrogen is passed through. When no more hydrogen chloride gas evolves, 9 g of water are added dropwise and stirring is again continued until evolution of hydrogen chloride gas ceases. The cyclohexane is then distilled off. The desired phosphoric acid monoester containing 12.2% of sulphur and 5.9% of phosphorus is thus obtained.

46 g of dioctylamine are added dropwise to 100 g of the sulphurised monoalkylphosphoric acid with stirring and cooling. The sulphurised monoalkylphosphoric acid monoamine salt is thereby obtained.

EXAMPLE 3

A mixture of allyl alcohol and diisobutylene is sulphurised and reacted to form the monophophoric acid ester monoamine salt as described in Example 1.

EXAMPLE 4

One part of the P-ester from Example 1 is mixed with 3 parts of sulphurised rape oil diisobutylene.

The efficiency of the high pressure additives according to the invention was tested on a gear wheel tension tester FZG according to DIN 51 354 sharpened with L-gear wheels and rotating at double speed. This procedure has been described by K. Seitzingen in "Schmiertechnik und Tribologie" 19 (1972) 22–29 as FZG L 16.6 90° C. In this test, the alloyed high pressure oil is used for lubricating a pair of gear wheels which is subjected to a progressively higher load by tensioning in 12 loading stages and rotated at 21,700 revs., in each case at an initial temperature of 90° C. After each loading stage, the pair of gear wheels is tested for wear by weighing and the flanks of the teeth are examined. The test is terminated when there are signs of seizing on the flanks of the teeth or a sudden sharp rise in the wear (sudden change into rapid wear condition). The better the quality of a high pressure oil, the larger are the number of loading stages which it will withstand and the lower is the wear, expressed in mg/PS x h. The test was made more stringent by carrying it out at the low alloying concentration of 2.5% in a low viscosity mineral oil of 8°E/50° C.

To assess the corrosiveness of the compounds, the Cu activity was determined according to ASTM-D-130. The corrosiveness is expressed in marks ranging from 1–4 subdivided into a, b and c.

| | FZG test | |
|---|---|---|
| Test results | Number of loading stages withstood | Specific wear mg/PS × h |
| 1) Commercial P-S additive based on phosphonate and thiophosphonate with sulphurised isobutylene | >12 | 0.52 |
| 2) Commercial P-S additive based on phosphoric acid ester amine salt with sulphurised ester olefine mixture | 11 | 0.12 |
| 3) Product from Example 1 | >12 | 0.27 |
| 4) Product from Example 4 | >12 | 0.25 |
| 5) P-S additive mixed from 1 part of monooctylphosphate monoamine salt and 3 parts of sulphurised rape oil diisobutylene | 9 | 0.25 |
| 6) 1 Part of dibutylphosphate amine salt and 3 parts of sulphurised rape oil diisobutylene | 8 | 0.39 |

Tests 1 and 2 show two trade products which have either high resistance to seizing or load carrying capacity combined with high wear, or poor load carrying capacity combined with good wear resistance.

The products according to the invention obtained according to Examples 1 and 4 show a marked improvement in that they combine high load carrying capacity with a balanced, low wear.

Test 5 shows the deterioration in the wear properties if the alkyl chain of the monoalkylphosphate is not sulphurised and Test 6 shows the further deterioration when dialkylester salts of phosphoric acid are used.

I claim:
1. Process for the preparation of a mixture of monoalkylphosphoric acid mono-salts of the formula

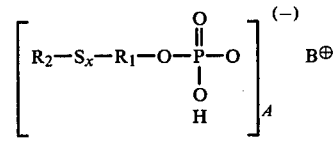

wherein
x represents a value of from 1 to 5,
B denotes a metallic or aminic cation,
A represents the valency of B, and
$R_1$ and $R_2$ are identical or different and denote straight chain, branched chain or cyclic, saturated or unsaturated, hydrocarbon groups having from 3 to 30 C-atoms which may be substituted by one or more of the following groups:
—OH, —COOH, —COOR$_6$, —OOCR$_6$, —OR$_6$,
[—O—PO(OH)—O]$^-$B$^\oplus$, —S$_x$—R$_6$
wherein R$^6$ denotes methyl, ethyl, R$^1$ of R$^2$, and B+ and x have the meaning given above.
comprising reacting two unsaturated hydrocarbons respectively bearing the radicals $R_1$ and $R_2$ and having 3 to 30 C-atoms with sulphur or a sulphur halide as a sulphurization agent, at least one of the hydrocarbons carrying at least one of the following groups:

—OH, —COOH, —COOR$_6$, —OOCR$_6$, —OR$_6$, [—O—PO(OH)—O]—B$^\oplus$, —S$_x$—R$_6$, thereafter phosphorylating the product of the sulphurization, and neutralizing the phosphorylation product with a base containing the cation B.

2. A mixture of monoalkylphosphoric acid monosalts produced by the process of claim 1.

3. A process according to claim 1, wherein one of the hydrocarbons is diisobutylene and the other carries a hydroxyl group, sulphurization is effected with sulphur, phosphorylation is effected with phosphorus pentoxide and the cation B is an aminic cation.

4. Process according to claim 1, characterized in that sulphurisation is carried out with sulphur chloride, half a mol of sulphur chloride being added for each double bond of the unsaturated compound at 0° to 100° C., followed by 1 mol of sodium sulphide per mol of sulphur chloride.

5. Process according to claim 1, characterized in that sulphurisation is carried out using elementary sulphur by heating to 120° to 200° C., 1 to 2 mols of sulphur being added per mol of unsaturated compound.

6. Process according to claim 1, wherein the unsaturated compound is an alcohol, phosphorylation is carried out at temperatures of from 20° to 150° C. after sulphurisation, using 1 mol of phosphorylating agent per mol of unsaturated compound, and thereafter hydrolysing at 20° to 100° C.

7. Process according to claim 1, characterized in that neutralisation of the monoalkylphosphoric acid is carried out with bases at temperatures of from 20° to 150° C., using stoichiometric quantities of base and monoester.

8. A mixture according to claim 1, wherein
X represents 2 or 3 and
A represents a value of from 1 to 3.

9. A mixture according to claim 1, in which
B denotes a metallic cation of elements 1 to 5 of the Main Group and 1 to 3 or 5 to 8 of the sub-Group of the Periodic System.

10. A process according to claim 1, in which B denotes an ammonium ion of the formula:

HN$^\oplus$R$_3$R$_4$R$_5$ wherein R$_3$, R$_4$ and R$_5$ denote hydrogen and/or identical or different straight chain or branched chain alkyl groups or cycloalkyl groups having from 1 to 30 C-atoms which may be substituted by ether, alcohol, amine or alkylamine groups.

* * * * *